United States Patent [19]

Starks

[11] 4,035,167

[45] July 12, 1977

[54] RECOVERY OF ETHANE AND ETHYLENE FROM GASEOUS MIXTURES

[75] Inventor: Charles M. Starks, Ponca City, Okla.

[73] Assignee: Continental Oil Company, Ponca City, Okla.

[21] Appl. No.: 657,994

[22] Filed: Feb. 13, 1976

[51] Int. Cl.² .......................................... B01D 51/06
[52] U.S. Cl. ........................................ 55/57; 55/84; 62/17; 62/20
[58] Field of Search ............... 62/17, 20; 55/68, 84, 55/37, 36, 46, 48, 63–65, 83, 88, 55, 57; 203/67, 68

[56] References Cited

U.S. PATENT DOCUMENTS

| | | | |
|---|---|---|---|
| 2,069,172 | 1/1937 | Miller | 62/17 |
| 2,433,286 | 12/1947 | McKinnis | 55/48 |
| 2,815,650 | 12/1957 | McIntire et al. | 55/48 |
| 2,970,177 | 1/1961 | Cobb | 55/65 |
| 3,016,985 | 1/1962 | Akin | 55/37 |
| 3,633,371 | 1/1972 | Davison | 62/17 |

*Primary Examiner*—Frank W. Lutter
*Assistant Examiner*—Frank Sever
*Attorney, Agent, or Firm*—Bayless E. Rutherford, Jr.

[57] ABSTRACT

A method for recovering ethane and ethylene from a gaseous mixture is disclosed. The method comprises: (1) contacting said gaseous mixture with a solvent to provide ethane- and ethylene-enriched solvent and (2) recovering from said enriched solvent said ethane and ethylene. The solvent used in the method is cyclohexane, cyclohexene, 1-chlorobutane, or 1,1,1-trichloroethane. The method is applicable also to recovering ethane and ethylene from methane containing these materials.

12 Claims, No Drawings

4,035,167

RECOVERY OF ETHANE AND ETHYLENE FROM GASEOUS MIXTURES

FIELD OF THE INVENTION

The invention is in the field of recovering ethane and ethylene from methane or gaseous mixtures which contain the materials.

BACKGROUND

Gasification of coal under pressure typically produces streams containing methane, carbon dioxide, carbonyl sulfide, hydrogen sulfide, plus small amounts of ethylene, ethane and other compounds. Usually, the concentration of ethane and ethylene is low (on the order of 1 to 2 volume percent) and cannot be easily separated by conventional methods. Because of their value it would be desirable to recover the ethane and ethylene. The concentration of ethane and ethylene can be increased by addition of aliphatic hydrocarbons into certain parts of the gasifier, yet even so one is still faced with their separation from a large amount of other gases. The present invention provides an improved method of recovering ethane and ethylene from gaseous mixtures.

PRIOR ART

A search of the prior art was conducted on the specific process of this invention. In addition, a search was conducted on the aspect of selective solvent absorption of hydrocarbons from a larger group of hydrocarbons. In reviewing the patents produced on the second search aspect, emphasis was directed to the particular solvents used in the process of the invention.

In the opinion of the agent preparing this application the most pertinent references are believed to be the following:

U.S. Pat. No. 2,573,341 teaches recovery of ethylene from a gaseous mixture containing a large proportion of methane and hydrogen by absorption in an aromatic distillate.

U.S. Pat. No. 3,633,371 teaches a process for recovering ethane from a normally gaseous material. The process used, as an absorbent, saturated hydrocarbons containing 4 to 8 carbons atoms. Normal hexane is preferred. The patent teaches that the absorption step is conducted at a temperature in the range of −70° to −120° F. This temperature is used to insure that the ethane and heavier materials are liquid.

In addition, numerous patents teach removal of "natural gasoline" from natural gas using an absorption liquid. U.S. Pat. No. 1,824,458 is typical of this art and teaches that the absorption liquid is a "hydrocarbon oil."

With regard to U.S. Pat. No. 3,633,771 data is presented herein which shows that cyclohexane gives better results than does hexane.

The remaining solvents used in the process of the invention are not taught in the prior art produced by the search.

BRIEF SUMMARY OF THE INVENTION

Briefly stated, the present invention is directed to a method for recovering ethane and ethylene from a gaseous mixture containing ethane and ethylene wherein said method comprises (1) contacting said gaseous mixture with a solvent to provide ethane- and ethylene-enriched solvent and (2) recovering from said enriched solvent said ethane and ethylene, said process being characterized further in that said solvent is selected from the consisting of cyclohexane, cyclohexene, 1-chlorobutane, and 1,1,1-trichloroethane.

In another embodiment, the present invention is directed to a method for recovering ethane and ethylene from methane containing ethane and ethylene using the method and solvents described in the preceding paragraph.

DETAILED DESCRIPTION

My invention is useful for recovering ethane and ethylene from methane or a gaseous mixture. When the method is used with methane substantially all of the gas, other than the ethane and ethylene will be methane. It is understood that minor amounts of impurities can be present.

The term gaseous mixture refers to a mixture containing methane, carbon dioxide, carbon monoxide, carbonyl sulfide, hydrogen sulfide and small amounts of other compounds containing the elements carbon, hydrogen, oxygen, and sulfur.

The combined amount of ethane and ethylene present in either the gaseous mixture or methane is usually in the range of about 0.05 to about 15 volume percent. More usually, the combined amount of ethane and ethylene is in the range of about 0.1 to about 3.0 volume percent.

Solvents which are useful in the method of my invention include the following: cyclohexane, cyclohexene, 1-chlorobutane, and 1,1,1-trichloroethane. In this connection it should be noted that the following materials give inferior results, and are therefor not considered useful, in the method of my invention: methanol, n-methylpyrrolidone, triethylene glycol, kerosene, dioctylphthalate, nitrobenzene, 1,2-dichloroethane, N,N-dimethylformamide, 1,4-dichlorobutane, 1,1,2-trichloroethane, 2-chloroethanol, and 1-decanol.

In conducting my process a suitable amount of solvent per total quantity of gas is in the range of about 0.01 to about 10 liters of liquid solvent per mole of total gas. On the same basis the preferred amount of solvent is about 0.1 to about 1 liters of liquid solvent.

Knowing that ethane and ethylene are removed from the gaseous mixture by contacting with the solvents used any person skilled in the art can determine the optimum method of conducting the contacting step. Preferably, the contacting is done by passing the gaseous mixture through one or more multi-stage absorption columns containing the solvent. When using an absorption column preferably the following conditions are maintained: a temperature in the range of about −30° to about 50° C. and a pressure of about 3 to about 140 atmospheres.

While not necessary, it is preferable that the major amount of the hydrogen sulfide, carbon dioxide, and carbonyl sulfide be removed from the gaseous mixture prior to contacting with the solvents used. Absorption methods for removal of hydrogen sulfide, carbonyl sulfide and carbon dioxide are well-known in the art and need not be described here. If these materials are not removed previously they will be present in minor amounts in the preferred solvent along with the ethane and ethylene.

The ethane and ethylene can be recovered from the solvents by any of several means. For example, release of pressure will release the ethane and ethylene. Also, heating the solvent will release the ethane and ethylene.

In order to disclose the nature of the present invention more specifically, the following examples will be given. It is to be understood that the invention is not to be limited to the specific conditions or details set forth in these examples except insofar as these limitations are specified in the appended claims.

The apparatus and method use for determining the equilibrium coefficients for absorption of ethane and ethylene present in methane in various solvents were as follows. The apparatus consisted of two pressure bombs (25 ml size) having inlet valves. A line with valves and pressure gauges, connected the two pressure bombs. A sample port was connected to the line between the valves. The procedure was as follows: Bomb A (25 ml) was charged with 10 ml of the solvent to be tested, while Bomb B was charged with the gas to be tested. Bomb A was rapidly pressured from the gas in Bomb B until the pressure gauges were equal. Valves between the bombs were rapidly closed. The pressure in Bomb A dropped, rapidly with shaking, as gas was absorbed into the liquid. When the pressure became constant in Bomb A, a small sample of the gas from the bomb was removed and analyzed by gas chromatography. From this analysis, and the drop in pressure, the quantities of each of the gaseous components in the gas phase and in the liquid phase were calculated. Equilibrium constants, K, were calculated by the equation:

$$K = \frac{\text{moles of the gas in liquid phase}}{\text{moles of the gas in the gas phase}}$$

The equilibrium constants, K, for the solvents of the present invention are shown in Table 1.

TABLE 1

| Solvent | K (EQUILIBRIUM CONSTANT) | |
|---|---|---|
| | Ethylene | Ethane |
| Cyclohexane | 2.2 | 3.2 |
| Cyclohexane | 2.1 | 2.7 |
| 1-Chlorobutane | 2.1 | 2.4 |
| 1,1,1-Trichloroethane | 2.2 | 2.7 |

A separate test was made to provide a comparison of equilibrium constants for cyclohexane and n-Hexane. The values obtained in this test are shown in Table 2.

TABLE 2

| Solvent | K VALUE | |
|---|---|---|
| | Ethylene | Ethane |
| Cyclohexane | 2.2 | 3.3 |
| n-Hexane | 1.1 | 2.0 |

For purpose of comparison the equilibrium constants on other materials tested are shown below.

TABLE 3

| Solvent | K (EQUILIBRIUM CONSTANT) | |
|---|---|---|
| | Ethylene | Ethane |
| Methanol | 1.4 | 1.2 |
| N-Methylpyrrolidone | 0.9 | 0.6 |
| Kerosene | 1.5 | 2.1 |
| 1,2-Dichloroethane | 1.5 | 1.3 |
| 1,1,2-Trichloroethane | 1.7 | 1.5 |

The removal of ethane and ethylene from a coal gasification stream using cyclohexane as the solvent is illustrated by the following example.

A mixture of hydrogen, carbon monoxide, methane, ethane, ethylene, carbon dioxide, hydrogen sulfide, and carbonyl suflide is taken from a coal gasification reactor. Ethane and ethylene, making up about 2 to 3 percent of this gas mixture, are separated from the gas by countercurrently conducting the gas, under 400 psig pressure, upward through a 5 stage column at a rate of 300 moles of total gas flow (as measured by the inlet gas volume, pressure and temperature) per 100 liters of cyclohexane extractant at room temperature. During this extraction more than 90% of the ethane and ethylene are taken from the gas phase into the cyclohexane and removed. These gases are removed from cyclohexane by depressuring and warming the cyclohexane solution.

The use of methanol, instead of cyclohexane, in the same process as the foregoing results in removal of only about half of the ethane and ethylene from the gas stream.

Thus, having described the invention in detail, it will be understood by those skilled in the art that certain variations and modifications may be made without departing from the spirit and scope of the invention as defined herein and in the appended claims.

I claim:

1. A method for recovering ethane and ethylene fom a gaseous mixture containing ethane and ethylene wherein said method comprises (1) contacting said gaseous mixture with a liquid phase solvent, selected from the group consisting of cyclohexene, 1-chlorobutane, and 1,1,1-trichloroethane, to absorb said ethane and ethylene from said mixture (2) desorbing by means of heating, depressurizing or a combination thereof, said ethane and ethylene.

2. The method of claim 1 wherein said contacting with solvent step is conducted at a temperature in the range of about −30° to about 50° C and a pressure of about 3 to about 140 atmospheres.

3. The method of claim 2 wherein said gaseous mixture contains about 0.05 to about 15 volume percent ethane and ethylene.

4. The method of claim 3 wherein said solvent is cyclohexene.

5. The method of claim 3 wherein said solvent is 1-chlorobutane.

6. The method of claim 3 wherein said solvent is 1,1,1-trichloroethane.

7. A method for recovering ethane and ethylene from methane containing ethane and ethylene wherein said method comprises (1) contacting said methane with a liquid phase solvent, selected from the group consisting of cyclohexene, 1-chlorobutane, and 1,1,1-trichloroethane, to absorb said ethane and ethylene from said mixture and (2) desorbing by means of heating, depressurizing or a combination thereof said ethane and ethylene.

8. The method of claim 7 wherein said contacting with solvent step is conducted at a temperature in the range of about −30° to about 50° C and a pressure of about 3 to about 140 atmospheres.

9. The method of claim 8 wherein said methane contains about 0.05 to about 15 volume percent ethane and ethylene.

10. The method of claim 9 wherein sid solvent is cyclohexane.

11. The method of claim 9 wherein said solvent is 1-chlorobutane.

12. The method of claim 9 wherein said solvent is 1,1,1-trichloroethane.

* * * * *

UNITED STATES PATENT OFFICE
CERTIFICATE OF CORRECTION

PATENT NO. : 4,035,167
DATED : July 12, 1977
INVENTOR(S) : Charles M. Starks

It is certified that error appears in the above-identified patent and that said Letters Patent are hereby corrected as shown below:

Column 1, line 44, "used" should be --uses--.

Column 3, Table I, under heading Solvent, "Cyclohexane", second occurrence, should be --Cyclohexene--.

Claim 1, Column 4, line 24, "fom" should be --from--.

Claim 10, Column 4, line 62, "sid" should be --said--.

Claim 10, Column 4, line 63, "cyclohexane" should be --cyclohexene--.

Signed and Sealed this

Eleventh Day of October 1977

[SEAL]

Attest:

RUTH C. MASON
Attesting Officer

LUTRELLE F. PARKER
Acting Commissioner of Patents and Trademarks